United States Patent [19]

Goldman et al.

[11] Patent Number: 5,417,980
[45] Date of Patent: May 23, 1995

[54] PHARMACEUTICAL COMPOSITIONS AND METHODS FOR TREATING THE SYMPTOMS OF OVERINDULGENCE

[75] Inventors: William J. Goldman, Ambler; Thomas N. Gates, Doylestown, both of Pa.

[73] Assignee: McNeil-PPC, Inc., Milltown, N.J.

[21] Appl. No.: 268,865

[22] Filed: Jun. 29, 1994

Related U.S. Application Data

[60] Continuation of Ser. No. 46,534, Apr. 13, 1993, abandoned, which is a division of Ser. No. 876,824, Apr. 29, 1992, Pat. No. 5,204,118, which is a continuation of Ser. No. 430,837, Nov. 2, 1989, abandoned.

[51] Int. Cl.$^6$ ............................................. A61K 9/20
[52] U.S. Cl. .................................. 424/464; 424/441; 514/810; 514/811; 514/926; 514/927
[58] Field of Search ................ 424/464, 441; 514/810, 514/811, 926, 927

[56] References Cited

U.S. PATENT DOCUMENTS

| | | | |
|---|---|---|---|
| 4,554,276 | 11/1985 | LaMattina | 514/272 |
| 4,676,984 | 6/1987 | Wu et al. | 424/157 |
| 4,704,728 | 11/1987 | Wu et al. | 424/157 |
| 4,757,060 | 7/1988 | Lukacsko et al. | 514/160 |
| 4,766,117 | 8/1988 | Crawford et al. | 514/219 |
| 4,880,804 | 11/1989 | Carini et al. | 514/253 |
| 5,204,118 | 4/1993 | Goldman et al. | 424/489 |

FOREIGN PATENT DOCUMENTS

| | | |
|---|---|---|
| 2105193 | 9/1982 | United Kingdom . |
| WO85/03443 | 8/1985 | WIPO . |

OTHER PUBLICATIONS

Friedman, L. S., and K. J. Isselbacher: Indigestion in *Harrison's Principles of Internal Medicine,* 11th Edition, 1986, McGraw Hill Book Company, N.Y., pp. 171–175.
Glass, G. B. J. L. Slomiany and A. Slomiany,: Biochemical and Pathological Derangements of the Gastrointestinal Tract following Acute and Chronic Ingestion of Ethanol in *Biochemistry and Pharmacology of Ethanol,* 1979, Plenum Press, N.Y., vol. 1, pp. 551–586.
Ritchie, J. M.: The Aliphatic Alcohols in Goodman and Gilman, *The Pharmacological Basis of Therapeutics,* 7th Edition, 1985, MacMillan Publishing Co., N.Y., pp. 375–386.
Lorber, S. H., and V. P. Dimoso, Jr.: Diseases of the Gastrointestinal Tract in *The Biology of Alcoholism,* vol. 3: Clinical Pathology, 1974 Plenum Press, N.Y., pp. 339–357.
Adams, R. D. and J. B. Martin: Headache in *Harrison's Principles of Internal Medicine,* 11th Edition, 1986, McGraw Hill Book Company, N.Y., pp. 26–33.
Seegers, A. J. M. L. P. Jager, and J. Van Noordwijk: Effects of Phenacetin Parcetamol and Caffeine on the Erosive Activity of Acetylsalicylic Acid in the Rat Stomach: Dose-Response Relationships, Time Course of Erosion Development and Effects of Acid Secretion, J. Pharm, Pharmacol 31:840–848, 1979.
Stern, A. I., D. L. Hogan, L. H. Kahn, and J. I. Isenberg: Protective Effect of Acetaminophen Against Aspirin—and Ethanol-Induced Damage to the Human Gastric Mucosa. Gastroenterology 86:728–733, 1984.
Deykin, D., P. Janson, and L. McMahon: Ethanol Potentiation of Aspirin-Induced Prolongation of the Bleeding Time. NEJM 306:852–854, 1982.
Unlisted Drugs, vol. 20, No. 11, Nov. 1968, Chatham, N.J., US p. 167, paragraph e: "Infacete".

*Primary Examiner*—Thurman K. Page
*Assistant Examiner*—James M. Spear
*Attorney, Agent, or Firm*—Bernard F. Plantz

[57] ABSTRACT

This invention relates to a pharmaceutical composition for treating the symptoms of overindulgence comprising an analgesic effective amount of acetaminophen or a non-steroidal anti-inflammatory drug and a gastric acid inhibiting effective amount of an $H_1$ or $H_2$ blocker, proton pump inhibitor or a combination thereof and methods of treating the symptoms of overindulgence comprising administering such pharmaceutical compositions.

7 Claims, No Drawings

PHARMACEUTICAL COMPOSITIONS AND METHODS FOR TREATING THE SYMPTOMS OF OVERINDULGENCE

This is a continuation of application Ser. No. 08/046,534, filed Apr. 13, 1993, now abandoned, which is division of application Ser. No. 07/876,824, filed Apr. 29, 1992, now U.S. Pat. No. 5,204,118, which is a continuation of application Ser. No. 07/30,837, filed Nov. 2, 1989, now abandoned. All of these applications are hereby incorporated by reference.

FIELD OF THE INVENTION

This invention relates to pharmaceutical compositions for treating the symptoms of overindulgence. More particularly, the invention comprises treating the symptoms of overindulgence with a combination of non-steroidal anti-inflammatory drug or acetaminophen and a histamine receptor blocker and/or a proton pump inhibitor composition.

BACKGROUND OF THE INVENTION

Non-steroidal anti-inflammatory drugs (hereinafter referred to as "NSAID(S)") and acetaminophen (hereinafter referred to as "APAP") are known to be effective analgesics for the treatment of mild to moderate pain. Histamine receptor blockers (referred to generically herein as $H_1$ or $H_2$ blockers) are effective inhibitors of gastric acid production. Proton pump inhibitors have been recently introduced as effective gastric acid inhibitors.

The symptoms of overindulgence due to excessive or inappropriate intake of food and/or alcoholic beverage are well known and include headache as well as indigestion, upper abdominal discomfort, bloating, heartburn or pyrosis. These latter symptoms collectively are sometimes referred to as acid indigestion or sour stomach. Indigestion has been variously described and will be defined herein as encompassing one or more of the following symptoms: abdominal pain and/or pressure, heartburn, a sense of abdominal fullness or bloating, excessive belching or flatulence and a vague feeling that digestion has not proceeded naturally (See Friedman, L. S., and K. J. Isselbacher, "Indigestion", *Harrison's Principles of Internal Medicine*, 11th Edition, McGraw Hill Book Company, N.Y., p 171–175, 1986).

The pathophysiology of indigestion is generally believed to be related to increased intraluminal acidity. The effects of alcohol and/or food on the gastrointestinal tract are influenced by a number of factors, including the mental state of the patient, the amount and type of food concurrently ingested, the individual subject's tolerance for alcohol and the presence or absence of disease. Gastric secretions stimulated by alcohol are rich in acid and normal in pepsin content. Stimulation of the antral mucosa by alcohol also leads to increased gastric secretion. Histamine has also been shown to be released in response to the alcohol-gastrin inter-relationship. (See Glass, G. B. J., B. L. Slomiany and A. Slomiany, "Biochemical and Pathological Derangements of the Gastrointestinal Tract following Acute and Chronic Ingestion of Ethanol", *Biochemistry and Pharmacology of Ethanol*, Vol 1, Plenum Press, N.Y., p 551–586, 1979.)

Alcohol in concentrations of about 10% in the stomach results in an acid rich secretion. Alcoholic drinks of 40% concentration and over are quite irritating to the gastric mucosa and cause congestive hyperemia and inflammation of the gastric mucosa and can produce erosive gastritis (See Ritchie, J. M., "The Aliphatic Alcohols", *The Pharmacological Basis of Therapeutics*, 7th Edition, MacMillan Publishing Co, N.Y., p 372–386, 1985). The irritation produced by alcohol stimulates sensitized visceral afferent nerves which accompany the abdominal sympathetic pathway and is responsible for the symptom of abdominal discomfort which accompanies overindulgence. Inflammation also generally lowers the threshold for pain from visceral distention or exaggerated muscular contraction (See Lorber, S. H., and V. P. Dimoso, Jr., "Diseases of the Gastrointestinal Tract", *The Biology of Alcoholism*, Vol 3, Clinical Pathology, Plenum Press, N.Y., p 339–357, 1974).

Heartburn or pyrosis is frequently associated with overindulgence and is the result of reflux of acidic gastric content into the lower esophagus after a large meal or excessive alcohol intake. Heartburn is described as a sensation of warmth or burning located substernally or high in the epigastrum with occasional radiation into the neck and occasionally to the arms.

Treatment of the gastric mucosal irritation and heartburn associated with overindulgence due to alcohol has traditionally been directed toward reducing gastric acidity with various oral antacids. Recent introduction of $H_2$ receptor blocking agents has added another dimension to the treatment regimen and has only lately been considered as a routine therapy for gastric mucosal irritation due to a variety of causes. Histamine is known to stimulate the release of gastric acid. Evidence is available that blocking the histamine gastric response is possible with agents which selectively block the $H_1$ receptor. Similarly, combinations of $H_1$ and $H_2$ receptor blocking agents have been shown to have a synergistic effect on protecting the gastric mucosa. An appropriate treatment of heartburn or pyrosis could encompass a composition containing an $H_1$ receptor blocking agent, an $H_2$ receptor blocking agent or a combination of the two depending upon the desired result or severity of the condition.

Headache due to excessive food or alcohol ingestion is a much more obscure subject. While the etiology of the common headache due to overindulgence may be related to the essential oils, metabolic by-products of ethyl alcohol metabolism or osmotic changes induced by the anhydrous nature of the alcohol itself, specific details of the mechanism are difficult to determine. Should etiologies and mechanisms of headache production be more precisely known, therapy can be more specifically oriented. Meanwhile, treatment has been directed at avoidance and symptomatic therapy with analgesic compositions, e.g. aspirin or APAP (See Adams, R. D. and J. B. Martin, "Headache", *Harrison's Principles of Internal Medicine*, 11th Edition, McGraw Hill Book Company, N.Y., p 26–33, 1986).

The treatment of the symptoms of overindulgence often requires the co-administration of an analgesic to relieve the headache along with an agent to reduce gastric acidity which is generally believed to cause the indigestion and heartburn. For example, effervescent products comprising aspirin or APAP combined with an antacid such as sodium or calcium carbonates have been commercially available as treatments for the symptoms of overindulgence.

The concept of combining an agent to reduce or inhibit the production of gastric acid with an analgesic in a single composition has, however, heretofore been overlooked as a method of treating overindulgence. Such a combination would be a significant advance and meet a long felt need for treating the symptoms of overindulgence, permitting a single composition to more effectively treat all the symptoms concurrently.

SUMMARY OF THE INVENTION

The foregoing object of fulfilling a long felt need for pharmaceutical compositions which can relieve the symptoms of overindulgence defined herein as headache and acid indigestion has now been accomplished in accordance with the compositions and methods of the present invention.

In accordance with the purposes of the invention, as embodied and fully described herein, the invention comprises pharmaceutical compositions and methods for treating the symptoms of overindulgence comprising an analgesic effective amount of an NSAID or APAP and a gastric acid inhibiting effective amount of an $H_1$ or $H_2$ blocker, or a proton pump inhibitor or a combination thereof.

In preferred embodiments the NSAID is selected from the group consisting of propionic acid derivatives including ibuprofen, fenoprofen, naproxen and ketoprofen; fenamic acid derivatives, including meclofenamate and mefenamic acid; oxicams, including piroxicam; indole acetic acids, including indomethacin, sulindac, tolmetin; and pharmaceutically acceptable salts thereof. The preferred $H_1$ or $H_2$ or proton pump inhibitors are selected from the group consisting of the $H_2$ receptor blocking drugs cimetidine, ranitidine and famotidine; the proton pump inhibitor drug omeprazole; and the $H_1$ receptor blocking drugs, from the group ethanolamines including diphenhydramine, dimenhydrinate, carbinoxamine, from the group ethylenediamines, including tripelennamine, pyrilamine, from the group alkylamines, including chorpheniramine, from the group piperazines, including hydroxyzine, cyclizine, meclizine, from the group phenothiazines, including promethazine. In more preferred embodiments the APAP or ibuprofen are used in combination with cimetidine.

As embodied and broadly described herein, the invention further comprises a method for treating the symptoms of overindulgence comprising administering a combination pharmaceutical composition to a patient comprising an analgesic effective amount of APAP or an NSAID and a gastric acid inhibiting effective amount of an $H_1$ or $H_2$ blocker, or a proton pump inhibitor or a combination thereof as is described above.

DETAILED DESCRIPTION OF PREFERRED EMBODIMENTS OF THE INVENTION

Reference will now be made in detail to preferred embodiments of the invention, examples of which are illustrated in the following examples section.

To achieve the object of the invention of providing a pharmaceutical composition for treating the symptoms of overindulgence an analgesic effective amount of APAP or an NSAID is combined with a gastric acid inhibiting effective amount of an $H_1$ or $H_2$ blocker or a proton pump inhibitor or a combination thereof.

The treatment of overindulgence with the combinations of the invention which combine gastric acid inhibiting amounts of $H_1$ or $H_2$ blocker or a proton pump inhibitor or a combination thereof with such NSAIDs is directed to the symptomatic relief of the complaints of acid indigestion and headache. This requires the use of an agent which would treat the headache, abdominal discomfort and reduce the intraluminal gastric acidity. Since no single agent has been found to be capable of treating the multiple symptoms of overindulgence, a composition such as is described in this invention is recommended.

APAP, a well-known clinically proven analgesic and antipyretic, produces analgesia by elevating the pain threshold. APAP is indicated as an analgesic for both acute and chronic pain conditions, including arthritic and rheumatic conditions involving musculoskeletal pain, headache, dysmenorrhea, myalgias and neuralgias. APAP is an extremely safe analgesic, rarely producing side-effects and is especially well tolerated by aspirin-sensitive patients. (Seegers, A. J. M., L. P. Jager, and J. Van Noordwijk, "Effects of Phenacetin Parcetamol and Caffeine on the Erosive Activity of Acetylsalicylic Acid in the Rat Stomach: Dose-Response Relationships, Time Course of Erosion Development and Effects of Acid Secretion", *J. Pharmacol,* 31:840–848, 1979), have shown that APAP decreases the gastric erosive activity of a strongly ulcerogenic NSAID. (Stern, A. I., D. L. Hogan, L. H. Kahn, and J. I. Isenberg, "Protective Effect of Acetaminophen Against Aspirin—and Ethanol-Induced Damage to the Human Gastric Mucosa", *Gastroenterology,* 86:728-733, 1984), have additionally shown that a single dose of APAP prevents a significant amount of gastric mucosal damage caused by both aspirin and alcohol. Further, APAP is particularly well suited as an analgesic in patients with hemostatic disturbances as well as in patients with upper gastrointestinal disorders including ulcers, gastritis and hiatus hernia.

Aspirin and other NSAIDs are commonly used for the treatment of pain and inflammation of a variety of etiologies. The mechanism of action of this class of drugs is by inhibition of the enzyme of prostaglandin synthetase, both centrally and peripherally. The peripheral prostaglandin synthetase inhibiting activity of aspirin and other NSAIDs is responsible for the anti-inflammatory and analgesic activity as well as for many of the varied side-effects of these drugs. Aspirin is specifically excluded from this invention since aspirin, by itself, causes severe inflammation of the gastric mucosa. In the presence of alcohol, this effect of aspirin is enhanced. Similarly, prolongation of bleeding time induced by aspirin, is enhanced in the presence of alcohol (See Deykin, D., P. Janson and L. McMahon, "Ethanol Potentiation of Aspirin-Induced Prolongation of the Bleeding Time", *New England Journal of Medicine,* 306:852-854, 1982). For these reasons aspirin is not a rational choice either alone or in combination with other compositions for treating acid indigestion in general and as it relates to overindulgence. While other NSAIDs can by themselves lead to increased stomach upset, this effect is not as severe as with aspirin, and they are thus useful in treating the symptoms of overindulgence in accordance with the combination composition of the invention.

The presence of gastrin, acetylcholine and histamine in the stomach interacting with the histamine receptor on the parietal cell results in the increased secretion of hydrochloric acid. The activity of gastrin and acetylcholine are believed to be influenced by histamine. Inhibition of the histamine receptor prevents the attachment of histamine to the parietal cell and subsequently inhibits acid secretion. Omeprazole, a proton pump inhibitor, irreversibly inhibits the enzyme responsible for acid production.

The histamine receptors are differentiated by the class of inhibitor so that while the acid secreting histamine receptor is called an $H_2$ receptor with the inhibitors of this site being called the $H_2$ receptor blocker, the histamine $H_1$ receptor site blockers comprise another class of antihistamine drugs. The combination of $H_1$ and $H_2$ blockers can synergistically protect the gastrointestinal mucosa from the effects of chemically induced damage such as occurs in alcohol and food related overindulgence.

The composition of the present invention shall preferably contain a combination of the following compositions or their pharmaceutically acceptable salts either acetaminophen from 500 to 1000 mg per dose or one of several NSAIDs from the group of: propionic acid derivatives including ibuprofen (the term ibuprofen is meant to include administration of both the racemic mixture of R- and S-enantiomers and the substantially pure S-enantiomer which is the analgesic active form of ibuprofen) from 200 to 400 mg per dose; naproxen from 200 to 500 mg per dose; fenoprofen from 200 to 600 mg per dose; ketoprofen from 50 to 300 mg per dose, meclofenamate from 50 to 400 mg per dose, mefenamic acid from 250 to 500 mg per dose; piroxicam from 10 to 20 mg per dose; indomethacin from 25 to 200 mg per dose, sulindac from 150 to 400 mg per dose, tolmetin from 200 to 1200 mg per dose; in combination with the $H_2$ receptor blocking drugs including cimetidine from 150 to 800 mg per dose; ranitidine from 50 to 300 mg per dose; famotidine from 5 to 40 mg per dose; or in combination with the proton pump inhibitor drugs including omeprazole from 60 to 500 mg per dose; and/or an $H_1$ receptor blocking drug from the group ethanolamines including diphenhydramine 25 to 200 mg per dose; dimenhydrinate from 50 to 400 mg per dose, carbinoxamine from 4 to 8 mg per dose; from the group ethylenediamines including tripelennamine from 25 to 300 mg per dose; pyrilamine from 25 to 100 mg per dose; from the group alkylamines including chorpheniramine from 2 to 24 mg per dose, from the group piperazines including hydroxyzine from 25 to 100 mg per dose, cyclizine from 50 to 300 mg per dose, meclizine from 8 to 400 mg per dose; and from the group phenothiazines including promethazine from 12.5 to 50 mg per dose.

The dosage ranges described above are preferred adult doses and may vary depending upon the age and weight of the patient as would be known by those skilled in the pharmaceutical arts. Further, if a combination of, for example an $H_1$ and $H_2$ blocker is used, the dosage for each may be reduced.

To establish the efficacy of the composition of this invention in humans, patients suffering from the symptoms of overindulgence which will include any of the constellation of signs of indigestion, upper abdominal discomfort, bloating, heartburn or pyrosis and headache can be administered acetaminophen or a non-steroidal anti-inflammatory drug with and without histamine receptor blockers ($H_1$ and/or $H_2$ blocking agents). To determine efficacy, patients are asked to subjectively estimate onset of relief, duration of relief and time to maximum relief. Appropriate statistical methods are used to show that on the average, acetaminophen or non-steroidal anti-inflammatory agents with $H_1$ histamine and/or $H_2$ histamine receptor blocking drugs are more efficacious.

Since appropriate animal models for the evaluation of overindulgence are not available, studies will not be conducted involving laboratory animals.

Other ingredients both active and inactive can be added to the combination pharmaceutical compositions of the invention. For example, flavoring compositions are desirably added to chewable and liquid dosage forms. Further, antidiarrheal, antiflatulent, antispasmodic and/or anticholinergic compositions may be added to the compositions of the invention to reduce and relieve gastrointestinal distress, which may be associated with acid indigestion. Examples of antidiarrheals include loperamide, attapulgite, bismuth subsalicylate, diphenoxylate HCl, polycarbophil, calcium polycarbophil and mixtures thereof. An example of an antiflatulent is simethicone. Examples of antispasmodics include phenobarbital dicyclomine HCl, belladonna alkaloids, and atropine.

EXAMPLES

The invention will now be illustrated by examples. The examples are not intended to be limiting of the scope of the present invention but read in conjunction with the detailed and general description above, provide further understanding of the present invention and an outline of a process for preparing the compositions of the invention. Example 1–10 disclose various formulations for preparing tablets or caplets in accordance with the invention. Various conventional techniques for preparing medicament tablets or caplets can be employed as would be known to those skilled in the art as is disclosed for example by *Remington's Pharmaceutical Sciences*, Mack Publishing Co., Chapter 90, "Oral Solid Dosage Forms", pp. 1603–1632 (1985). The disclosure of this reference is hereby incorporated herein by reference.

Example 1

A tablet consisting of:
500 mg of acetaminophen;
150 mg of cimetidine; and
other auxiliary agents and coloring agents.

Example 2

A tablet consisting of:
500 mg of acetaminophen;
25 mg of diphenhydramine; and
other auxiliary agents and coloring agents.

Example 3

A tablet consisting of:
200 mg of ibuprofen;
150 mg of cimetidine; and
other auxiliary agents and coloring agents.

Example 4

A tablet consisting of:
200 mg of ibuprofen;
50 mg of ranitidine; and
other auxiliary agents and coloring agents.

Example 5

A tablet consisting of:
200 mg of ibuprofen;
25 mg of diphenhydramine; and
other auxiliary agents and coloring agents.

Example 6

A tablet consisting of:
500 mg of acetaminophen;
50 mg of ranitidine; and
other auxiliary agents and coloring agents.

Example 7

A tablet consisting of:
500 mg of acetaminophen;
150 mg of cimetidine;
25 mg of diphenhydramine; and
other auxiliary agents and coloring agents.

Example 8

A tablet consisting of:
200 mg of ibuprofen;
150 mg of cimetidine;
25 mg of diphenhydramine; and
other auxiliary agents and coloring agents.

Example 9

A tablet consisting of:
500 mg of acetaminophen;
50 mg of ranitidine;
25 mg of diphenhydramine; and
other auxiliary agents and coloring agents.

Example 10

A tablet consisting of:
200 mg of ibuprofen;
50 mg of ranitidine;
25 mg of diphenhydramine; and
other auxiliary agents and coloring agents.

Example 11

A tablet consisting of:
500 mg of acetaminphen;
60 mg of omeprazole; and
other auxiliary agents and coloring agents.

Example 12

A tablet consisting of:
200 mg ibuprofen;
60 mg omeprazole; and
other auxiliary agents and coloring agents.

Example 13

A tablet consisting of:
500 mg acetaminophen;
60 mg omeprazole;
25 mg diphenhydramine; and
other auxiliary agents and coloring agents.

Example 14

A tablet consisting of:
200 mg ibuprofen;
60 mg omeprazole;
25 mg diphenhydramine; and
other auxiliary agents and coloring agents.

Various other dosage forms can be applied herein such as a filled gelatin capsule, liquid emulsion/suspension or chewable tablet form employing the dosage actives provided above or other dosage amounts in accordance with the present invention. A liquid suspension of ibuprofen to which cimetidine, diphenhydramine, ranitidine or combinations thereof in the amounts provided above can be added to the ibuprofen suspension disclosed in co-pending U.S. patent application Ser. No. 372,734, the entire disclosure of this Patent Application is hereby incorporated herein by reference.

Method of Treating Patients for the Symptoms of Overindulgence

A patient exhibiting the symptoms or suffering from the symptoms of overindulgence is treated by the oral administration of one tablet of the pharmaceutical composition in accordance with any of Examples 1–10.

The scope of the present invention is not limited by the description, examples and suggested uses herein and modifications can be made without departing from the spirit of the invention. For example, the pharmaceutical compositions of the invention may be provided in a sustained release formulation for prolonged and/or nightime treatment of the symptoms of overindulgence. Application of the compositions and methods of the present invention for medical and pharmaceutical uses can be accomplished by any clinical, medical and pharmaceutical methods and techniques as are presently or prospectively known to those skilled in the art. Thus it is intended that the presently claimed invention cover the modifications and variations of this invention provided that they come within the scope of the appended claims and their equivalents.

What is claimed is:

1. A pharmaceutical composition for treating the symptoms of overindulgence due to the excessive or inappropritate intake of food and/or alcoholic beverages comprising in an oral tablet or caplet dosage form a therapeutically effective amount of an analgesic and a gastric acid inhibiting effective amount of a proton pump inhibitor wherein the therapeutically effective amount of the analgesic is selected from the group consisting of acetaminophen from 500 to 1000 mg per dose, ibuprofen from 200 to 400 mg per dose, naproxen from 200 to 500 mg per dose, fenoprofen from 200 to 600 mg per dose, ketoprofen from 50 to 300 mg per dose, meclofenamate from 50 to 400 mg per dose, mefenamic acid from 250 to 500 mg per dose, piroxicam from 10 to 20 mg per dose, indomethacin from 25 to 200 mg per dose, sulindac from 150 to 400 mg per dose, tolmetin from 200 to 1200 mg per dose and their pharmaceutically acceptable salts; in combination with an effective amount of the proton pump inhibitor omeprazole of from 60 to 500 mg per dose.

2. A pharmaceutical composition in accordance with claim 1 comprising a combination of ibuprofen and omeprazole.

3. A pharmaceutical composition in accordance with claim 1 comprising acetaminophen and omeprazole.

4. A pharmaceutical composition in accordance with claim 1 comprising a racemic mixture of R- and S-ibuprofen, substantially pure S-ibuprofen or naproxen and omeprazole.

5. A pharmaceutical composition in accordance with claim 1 wherein additionally there is present a therapeutically effective amount of an $H_1$ on $H_2$ receptor blocker selected from the group consisting of cimetidine from 150 to 800 mg per dose, ranitidine from 50 to 300 mg per dose, famotidine from 5 to 40 mg per dose, diphenhydramine 25 to 200 mg per dose, dimenhydrinate from 50 to 400 mg per dose, carbinoxamine from 4 to 8 mg per dose, tripelennamine from 25 to 300 mg per dose, pyrilamine from 25 to 100 mg per dose, chorpheniramine from 2 to 24 mg per dose, hydroxyzine from 25 to 100 mg per dose, cyclizine from 50 to 300 mg per dose, meclizine from 8 to 400 mg per dose and promethazine from 12.5 to 50 mg per dose.

6. A pharmaceutical composition in accordance with claim 1 comprising naproxen and omeprazole.

7. A pharmaceutical composition in accordance with claim 1 wherein the pharmaceutical is in chewable dosage form.

* * * * *